United States Patent [19]

Bochis et al.

[11] Patent Number: 4,482,545

[45] Date of Patent: Nov. 13, 1984

[54] ISOEFROTOMYCIN, PROCESS OF PREPARATION, PHARMACEUTICAL COMPOSITION AND METHOD OF USING SAME

[75] Inventors: Richard J. Bochis, East Brunswick; Ray S. Dewey, Martinsville, both of N.J.

[73] Assignee: Merck & Co., Inc., Rahway, N.J.

[21] Appl. No.: 541,804

[22] Filed: Oct. 13, 1983

[51] Int. Cl.$^3$ ................... A61K 31/71; C07H 3/06
[52] U.S. Cl. ................... 424/181; 424/180; 536/16.8; 536/18.1
[58] Field of Search ............... 424/180, 181; 536/16.8, 536/18.1

[56] References Cited

U.S. PATENT DOCUMENTS 4,024,251  5/1977  Maiese et al. ................... 536/16.8

OTHER PUBLICATIONS

Wax et al, "Chem. Abst." vol. 85, 1976, p. 92146(h).
*Tetrahedron Letters,* 5173 (1973), No. 52, Vos.

*Primary Examiner*—Johnnie R. Brown
*Attorney, Agent, or Firm*—David L. Rose; Mario A. Monaco

[57] ABSTRACT

There is disclosed the novel compound isoefrotomycin which is synthesized from efrotomycin as a Michael adduct by treatment with a mixture of polar and nonpolar solvents. Isoefrotomycin is an effective antimicrobial agent and growth promotant in animals.

10 Claims, No Drawings

ISOEFROTOMYCIN, PROCESS OF PREPARATION, PHARMACEUTICAL COMPOSITION AND METHOD OF USING SAME

BACKGROUND OF THE INVENTION

Efrotomycin is produced by the extraction of a fermentation broth of *Streptomyces lactamdurans*. The compound, the microoganism and the method used to obtain it are disclosed in U.S. Pat. No. 4,024,251 to Maise et al. Efrotomycin has the following structure:

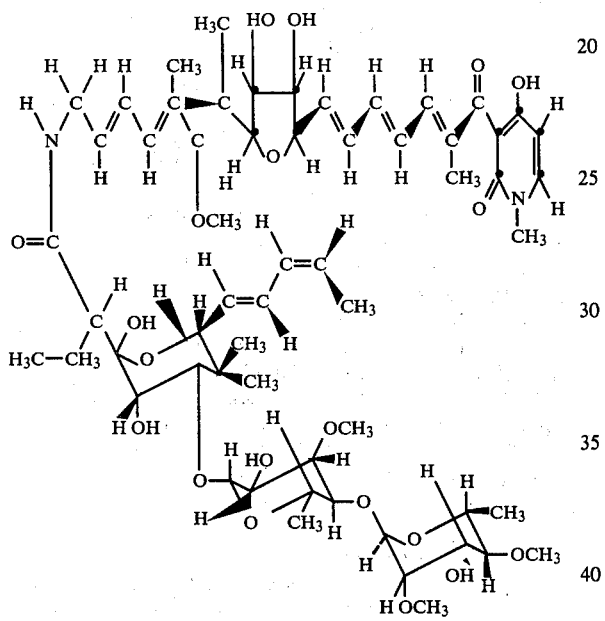

Efrotomycin is a Gram positive and Gram negative active antibiotic and antimicrobial agent and is useful as a growth promotant in domestic animals.

SUMMARY OF THE INVENTION

The instant invention is concerned with isoefrotomycin, a derivative of the natural product efrotomycin. Thus, it is an object of this invention to describe isoefrotomycin. It is a further object to describe the processes used to prepare isoefrotomycin. A still further object is to describe the use of isoefrotomycin as an antimicrobial agent and as a growth promotant. Further objects will become apparent from a reading of the following disclosure.

DESCRIPTION OF THE INVENTION

Isoefrotomycin is the Michael adduct of efrotomycin and has the following structure:

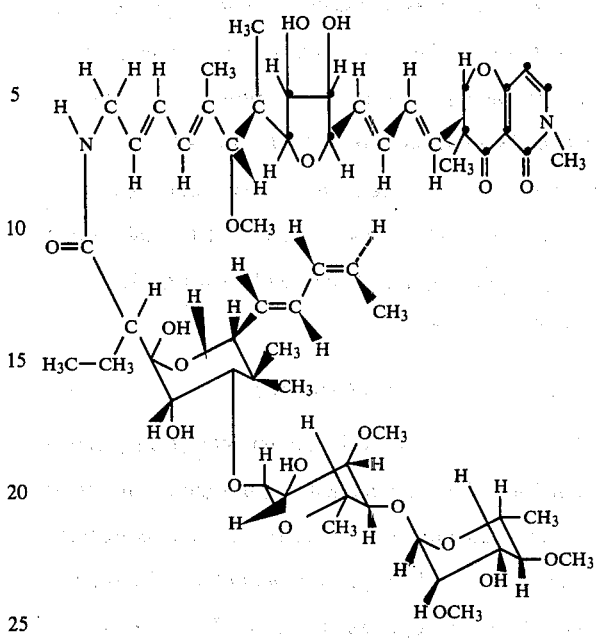

As is readily apparent, isoefrotomycin is the internal Michael adduct of efrotomycin which is formed by the connection of the 4-position hydroxy with the 9-position carbon atom. The Michael adduct reaction is an equilibrium reaction that is preferably carried out in a polar solvent-nonpolar solvent mixture at about room temperature although temperatures of from 15° to 30° C. have been successful. Reaction conditions which are generally used to shift a Michael adduct equilibrium towards the product such as acid or basic catalysis or high temperatures cannot be employed for isoefrotomycin since the efrotomycin and isoefrotomycin molecules are highly sensitive to pH and temperature changes deviating from neutral and room temperature respectively. Thus, the reaction is allowed to proceed to equilibrium at about room temperature for from 7 to 30 days whereupon the isoefrotomycin is isolated by removing the solvents and passing a mixture of efrotomycin and isoefrotomycin through a chromatography column eluting with a mixture of solvents. Multiple chromatographies are generally employed to obtain purified product.

Generally, in a solution of 17% methanol and 83% methylene chloride the equilibrium that is obtained consists of about 10% isoefrotomycin and 90% efrotomycin. Other polar solvents that can be employed in a Michael adduct equilibrium reaction are methanol, ethanol, propanol, isopropanol, and the like. Any nonpolar solvent such as chloroform, methylene chloride, dichloroethane, carbontetrachloride, and the like, may be employed. Generally, the solvent mixture consists of about 10 to 20% of the polar solvent and from about 90 to 80% of the nonpolar solvent.

In addition to its use as an antibiotic, isoefrotomycin is useful as a feed additive to promote the growth of animals such as chickens, sheep and cattle. The use of isoefrotomycin shortens the time required for bringing animals up to marketable weight. When isoefrotomycin is used as a growth promoter in animals it can be administered as a component of the feed or it may be dissolved or suspended in the drinking water.

Isoefrotomycin is administered in the same manner as is efrotomycin. The administration for antibiotic, antimicrobial uses as well as growth promotion uses is completely disclosed in U.S. Pat. No. 4,024,251 which is hereby incorporated by reference. The following example is being used to provide for a complete disclosure of the instant invention and must not be construed as being limitative thereof.

EXAMPLE 1

21 Grams of efrotomycin sodium salt was dissolved in a solution of 700 ml of methylene chloride and 100 ml of methanol and allowed to stand at room temperature for about six weeks. The reaction mixture was filtered and concentrated to dryness in vacuo. The residue was chromatographed on 800 g (1600 ml) of silica gel eluting with a mixture of 90 parts by volume of methylene chloride, 10 parts methanol and 1 part concentrated ammonium hydroxide. Fractions were taken at 20-ml volumes discarding fractions 1-59. Fractions 60-160 were combined and evaporated to dryness affording 5.44 g of residue which is placed on 550 g (1100 ml) of silica gel and diluted with the same 90:10:1 solvent system. Fractions were taken at 18-ml volumes discarding fractions 1-49. Isoefrotomycin is found in fractions 50-80 containing 2.918 g of the product. Isoefrotomycin has an Rf on silica gel and 90:10:1 methylene chloride:methanol:concentrated ammonium hydroxide (by volume) of 0.5 in a solvent system of 90:10 methylene chloride:methanol (by volume) the Rf is 0.45.

What is claimed is:

1. Isoefrotomycin having the following structure:

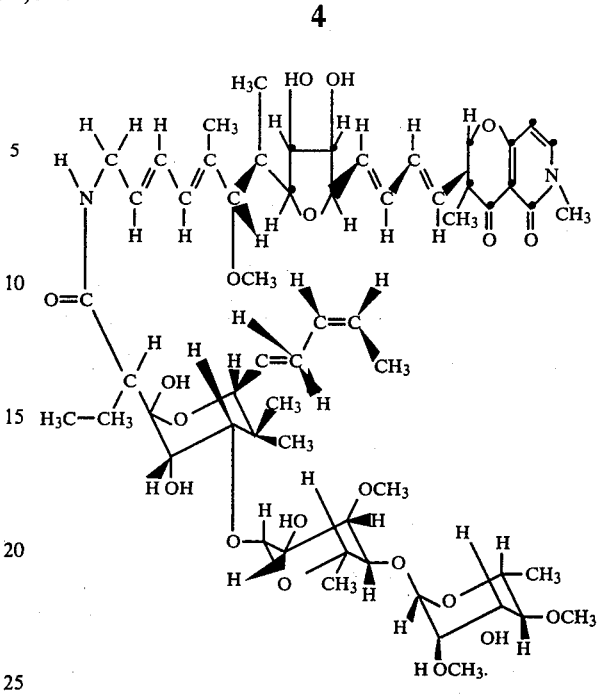

2. A process for the preparation of isoefrotomycin which comprises reacting efrotomycin in a mixture of polar and nonpolar solvents to cause the Michael adduct reaction between the 4-hydroxy and 9-carbon of efrotomycin.

3. The process of claim 2 wherein the reaction is carried out at from 15° to 30° C.

4. The process of claim 3 wherein the reaction is carried out at room temperature.

5. The process of claim 2 wherein the polar solvent is methanol, ethanol, propanol or isopropanol.

6. The process of claim 5 wherein the nonpolar solvent is methylene chloride, chloroform, dichloroethane or carbontetrachloride.

7. A composition comprising an antibacterially effective amount of isoefrotomycin and a nontoxic pharmaceutically acceptable excipient.

8. A composition for use in the growth promotion of chickens, sheep or cattle comprising a growth promoting amount of isoefrotomycin and inert carrier.

9. A method for combatting gram positive and gram negative bacterial infections which comprises contacting the area so infected with an effective amount of isoefrotomycin.

10. A method for the promotion of the growth of chickens, sheep or cattle which comprises the administration to such animals in feed or drinking water of an effective amount of isoefrotomycin.

* * * * *